(12) United States Patent
Galperin et al.

(10) Patent No.: US 10,709,314 B2
(45) Date of Patent: Jul. 14, 2020

(54) ENDOSCOPE TOOL POSITION HOLDER

(71) Applicant: Gyrus ACMI, Inc., Southborough, MA (US)

(72) Inventors: Nison Galperin, Fairfield, CT (US); Carlo A. DiRusso, Bronx, NY (US)

(73) Assignee: Gyrus ACMI Inc., Southborough, MA (US)

( * ) Notice: Subject to any disclaimer, the term of this patent is extended or adjusted under 35 U.S.C. 154(b) by 407 days.

(21) Appl. No.: 14/552,978

(22) Filed: Nov. 25, 2014

(65) Prior Publication Data

US 2015/0164307 A1    Jun. 18, 2015

Related U.S. Application Data

(60) Provisional application No. 61/915,007, filed on Dec. 12, 2013.

(51) Int. Cl.
| | |
|---|---|
| A61B 1/00 | (2006.01) |
| A61M 25/02 | (2006.01) |
| A61B 90/50 | (2016.01) |
| A61B 1/018 | (2006.01) |
| A61B 17/00 | (2006.01) |

(52) U.S. Cl.
CPC ...... *A61B 1/00128* (2013.01); *A61B 1/00066* (2013.01); *A61B 1/00133* (2013.01); *A61B 1/00147* (2013.01); *A61B 1/018* (2013.01); *A61B 17/00234* (2013.01); *A61B 90/50* (2016.02); *A61M 25/02* (2013.01); *A61B 2017/0034* (2013.01)

(58) Field of Classification Search
CPC .............. A61B 1/0014; A61B 1/00149; A61B 1/00121; A61B 1/0125; A61B 8/4218
USPC .......................................... 600/131, 113, 153
See application file for complete search history.

(56) References Cited

U.S. PATENT DOCUMENTS

| | | | |
|---|---|---|---|
| 842,505 A | 1/1907 | Unsinger | |
| 5,449,206 A * | 9/1995 | Lockwood | F16L 11/18 138/120 |
| 5,788,709 A | 8/1998 | Riek et al. | 606/114 |
| 5,899,425 A | 5/1999 | Corey, Jr. et al. | |
| 6,409,131 B1 * | 6/2002 | Bentley | A01K 97/10 248/219.4 |
| 7,717,846 B2 | 5/2010 | Zirps et al. | 600/104 |
| 7,922,650 B2 | 4/2011 | McWeeney et al. | 600/104 |

(Continued)

FOREIGN PATENT DOCUMENTS

| | | |
|---|---|---|
| EP | 2508120 A1 | 3/2007 |
| EP | 2329760 A1 | 6/2011 |

(Continued)

*Primary Examiner* — Alexandra L Newton
*Assistant Examiner* — Rynae Boler
(74) *Attorney, Agent, or Firm* — Harrington & Smith

(57) ABSTRACT

An apparatus including a first end configured to connect to a control of an endoscope object removal tool; a second end having a connector configured to removably connect to a handle of an endoscope; and a spine connecting the first end to the second end. The spine comprises a plurality of serially interconnected members which are rotatable relative to each other. Connections of the members to one another comprise friction locks. The friction locks are configured to be temporarily unlocked by overcoming friction forces at the friction locks such that the spine is semi-flexible.

20 Claims, 8 Drawing Sheets

(56) References Cited

U.S. PATENT DOCUMENTS

| | | | |
|---|---|---|---|
| 8,052,636 B2 | 11/2011 | Moll et al. | 604/95.04 |
| 8,190,238 B2 | 5/2012 | Moll et al. | 600/424 |
| 8,449,538 B2 | 5/2013 | Long | 606/41 |
| 2002/0177847 A1 | 11/2002 | Long | 606/46 |
| 2004/0015050 A1* | 1/2004 | Goto | A61B 18/1492 600/104 |
| 2005/0065399 A1* | 3/2005 | Sasaki | A61B 1/018 600/106 |
| 2005/0090835 A1 | 4/2005 | Deal et al. | |
| 2005/0272975 A1 | 12/2005 | McWeeney et al. | 600/113 |
| 2007/0129634 A1* | 6/2007 | Hickey | A61B 8/00 600/439 |
| 2007/0197896 A1 | 8/2007 | Moll et al. | 600/407 |
| 2008/0041394 A1 | 2/2008 | Swann et al. | |
| 2011/0213300 A1 | 9/2011 | McWeeney et al. | 604/95.04 |
| 2012/0172850 A1* | 7/2012 | Kappel | A61B 1/00149 606/1 |
| 2012/0191006 A1 | 7/2012 | Ostrovsky et al. | 600/562 |
| 2014/0171735 A1 | 6/2014 | Galperin et al. | 600/106 |

FOREIGN PATENT DOCUMENTS

| | | |
|---|---|---|
| GB | 1002076 A | 8/1965 |
| JP | H-04124101 A | 4/1992 |
| JP | H08 131441 A | 5/1996 |
| JP | H-1033536 A | 2/1998 |
| JP | 2001000384 A | 1/2001 |
| JP | 2004532064 A | 10/2004 |
| JP | 2005058749 A | 3/2005 |
| JP | 2007151595 A | 6/2007 |
| JP | 2008529723 A | 8/2008 |
| JP | 2013538099 A | 10/2013 |
| WO | WO-2013/078402 A2 | 5/2013 |

* cited by examiner

ENDOSCOPE TOOL POSITION HOLDER

CROSS-REFERENCE TO RELATED APPLICATION

This application claims priority under 35 USC 119(e) on U.S. provisional patent application No. 61/915,007 filed Dec. 12, 2013, which is hereby incorporated by reference in its entirety.

BACKGROUND

1. Technical Field

The exemplary and non-limiting embodiments relate generally to an endoscope and, more particularly, to a holder for holding a tool relative to an endoscope.

2. Brief Description of Prior Developments

Endoscopes are known which have a working channel to allow a tool to be extended to a distal end of the endoscope. Some tools can be attached to the endoscope housing with a clip-on device. However, existing devices having a clip-on device interfere with other accessories, occupy extra working space, and do not allow the surgeon to conveniently position when using the tool in a medical procedure. In addition, most of the times the surgeon cannot hold the tool as it was designed and often prefers not to use the clip-on device at all. There is also a big stress on the surgeon's wrist and waist when operating an endoscope handle to twist a flexible endoscope and a working tool separately. Thus, another surgeon or nurse must operate the tool. This makes the clinical procedure inefficient.

SUMMARY

The following summary is merely intended to be exemplary. The summary is not intended to limit the scope of the claims.

In accordance with one aspect, an example embodiment is provided in an apparatus including a first end configured to connect to a control of an endoscope object removal tool; a second end having a connector configured to removably connect to a handle of an endoscope; and a spine connecting the first end to the second end. The spine comprises a plurality of serially interconnected members which are rotatable relative to each other. Connections of the members to one another comprise friction locks. The friction locks are configured to be temporarily unlocked by overcoming friction forces at the friction locks such that the spine is semi-flexible.

In accordance with another aspect, an example method comprises providing a spine comprising a plurality of serially interconnected members which are rotatable relative to each other, where connections of the members to one another comprise friction locks, where the spine is semi-rigid and is reconfigurable to different semi-rigid shapes; connecting a first connector to a first end of the spine, where the first connector is sized and shaped to removably connect to a control of an endoscope object removal tool; and connecting a second connector to an opposite second end of the spine, where the second connector is sized and shaped to removably connect to a handle of an endoscope.

In accordance with another aspect, an example method comprises connecting a first end of an accessory to a handle of an endoscope; connecting a second end of the accessory to a control of an endoscope object removal tool; and reconfiguring a shape of a semi-rigid spine of the accessory from a first configuration to a second configuration, where the semi-rigid spine connects the first end to the second end, and where the semi-rigid spine retains the relative location of the first and second ends at the first configuration and retains the relative location of the first and second ends at the second configuration.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
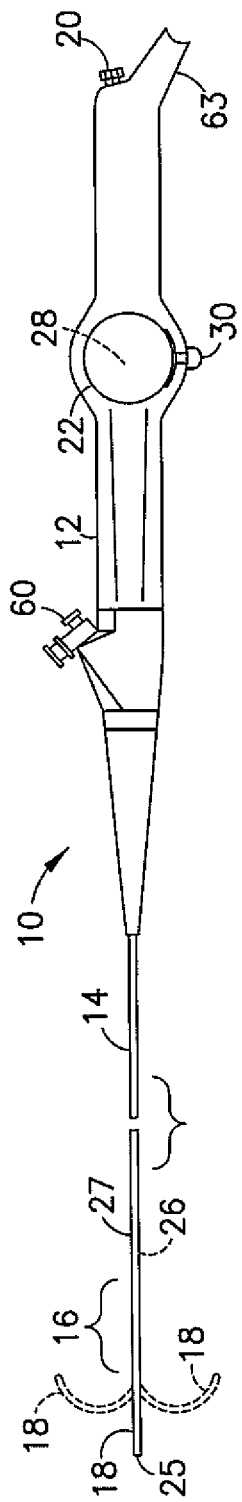
FIG. 1 is a side elevation view of an endoscope.

Referring to FIG. 1, there is shown a side view of an endoscope 10. Although the invention will be described with reference to the example embodiments shown in the drawings, it should be understood that the invention can be embodied in many alternate forms of embodiments. In addition, any suitable size, shape or type of elements or materials could be used.

The endoscope 10 is a ureteroscope. However, in alternate embodiments the endoscope could be any suitable type of endoscope. The endoscope 10 generally comprises a handle or control 12 and a flexible or semi-flexible shaft 14 connected to the handle 12. The shaft 14 includes a passive deflection section 16 and an active deflection section 18 at the distal end of the shaft 14. A control system 22 to control the active deflection section 18 extends from the handle 12 to the active deflection section 18. The control system 22 generally comprises a pair of control wires or at least one control wire, two wire sheaths, and an actuator 28. The wires are connected to the actuator 28 at one end and are connected to the active deflection section 18 at a second end.

In the preferred embodiment, the handle 12 has a user operated slide or lever 30. The lever 30 is connected to the actuator 28. The actuator 28 is adapted to pull and release the two wires of the control system 22. When the lever 30 is moved by the user, the actuator is moved. The actuator 28 may be a drum or pulley rotatably connected to the handle 12 to pull one wire while optionally releasing the other. In an alternate embodiment, the actuator may be any suitable type of device, such as a rocker arm adapted to pull and release the wires of the control system 22. In another alternate embodiment, where the control system may have two or more pairs of control wires, the handle may have additional actuators and corresponding controls to drive the additional pairs of control wires. In still other alternate embodiments, the handle may have knobs with rack and pinion mechanisms or other suitable user operated controls for the control system.

The shaft 14 is cantilevered from the handle 12. The shaft 14 generally comprises a frame 26, a cover 27 and an objective head 25. The shaft 14 includes the control wires of the control system 22, a fiber optical image bundle or electrical sensor cable, at least one fiber optical illumination bundle, and a working channel. A port 60 for inserting a working tool or instruments into the working channel is located on the handle 12. The proximal end of the handle 12 includes a connector 20 as further described below. In addition, the handle 12 has an electrical cable 63 for connection to another device, such as a video monitor. In an alternate embodiment, instead of the cable 63, the endoscope could have an eyepiece. In alternate embodiments, the flexible shaft may house different systems within.

Figure 2:
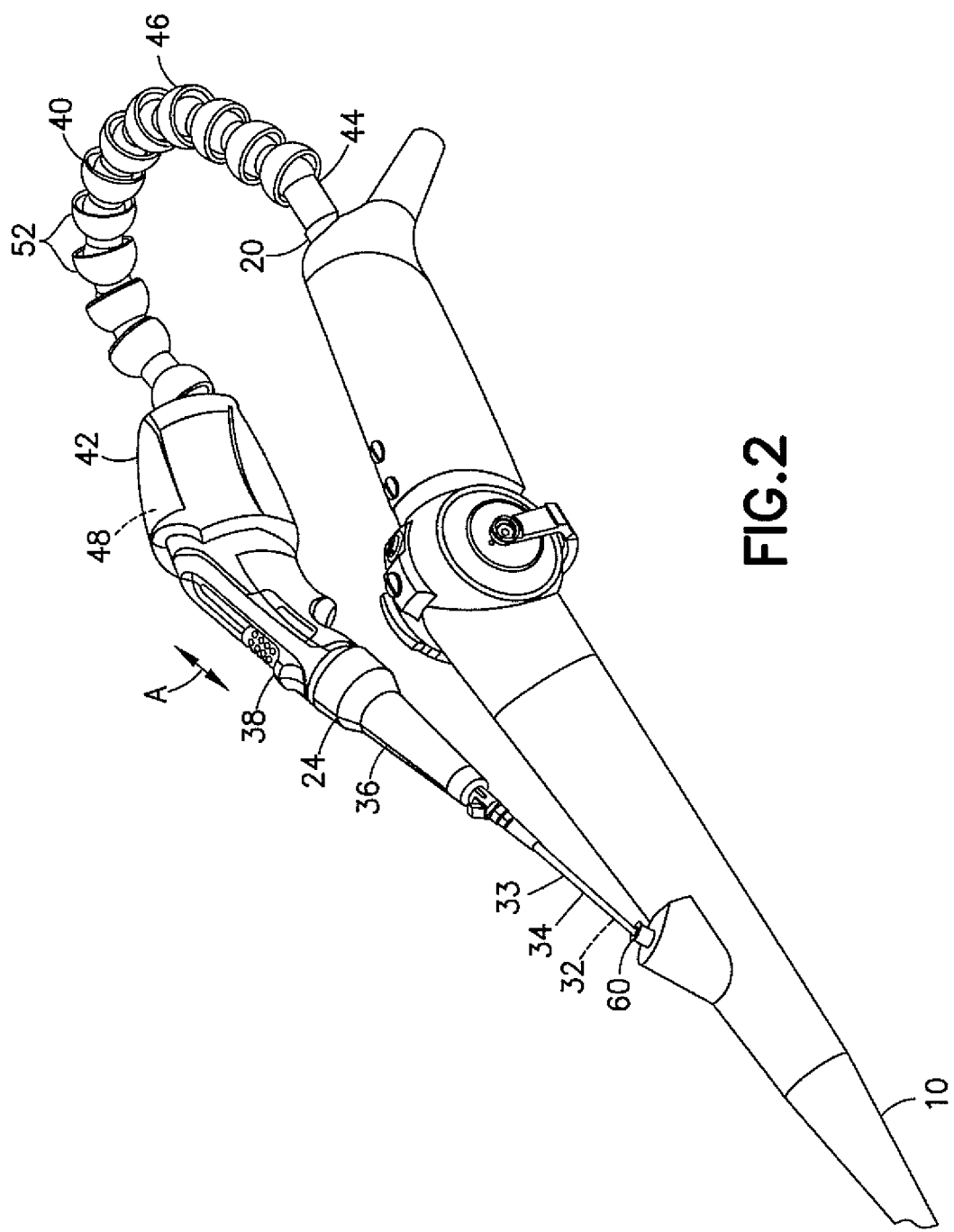
FIG. 2 is a partial perspective view of the endoscope shown in FIG. 1 having a working tool and position holder connected thereto.
Figure 3:
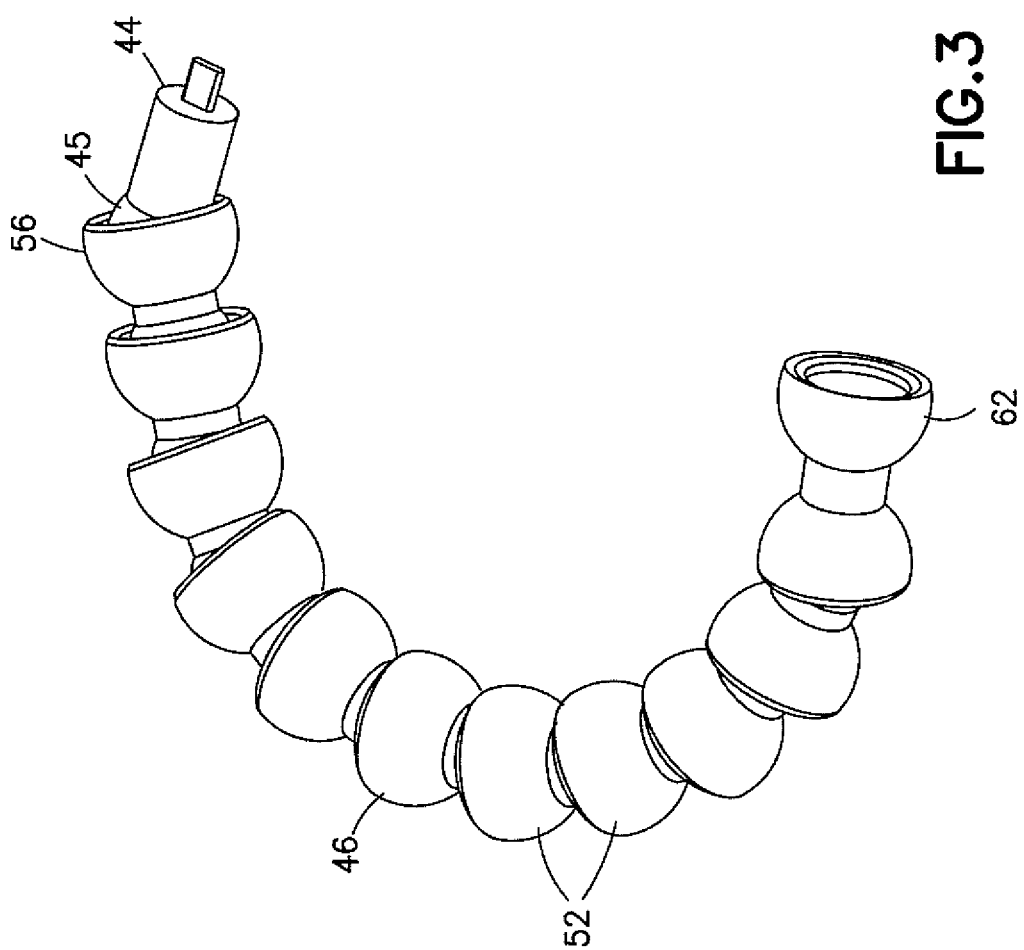
FIG. 3 is a perspective view of a spine of the holder shown in FIG. 2.
Figure 4:
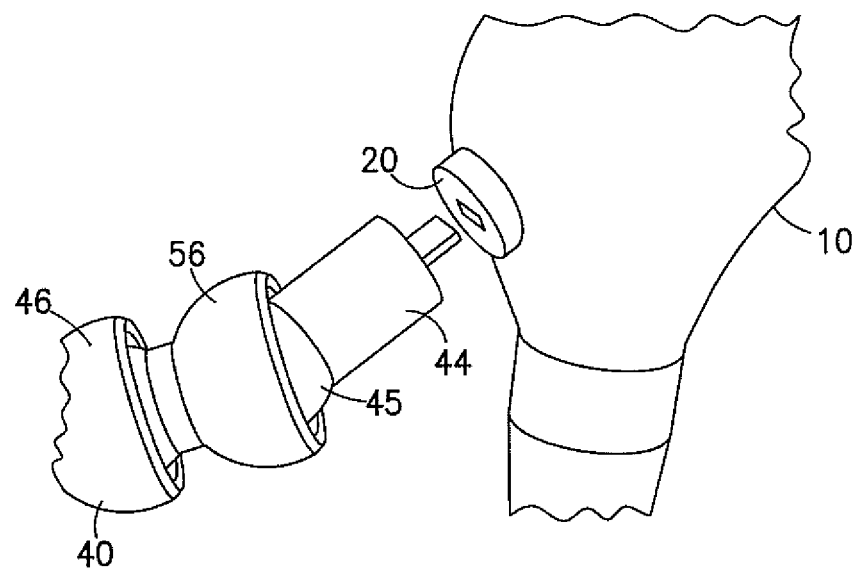
FIG. 4 is a partial perspective view of a connection of the holder to the endoscope shown in FIG. 2.
Figure 5:
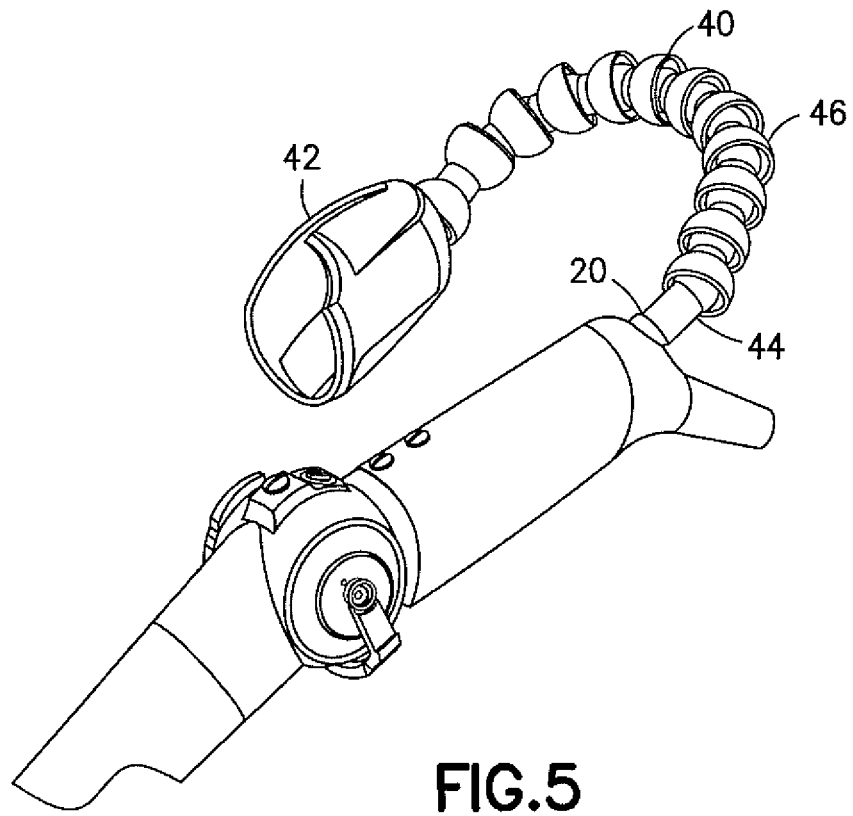
FIG. 5 is a perspective view of the holder and a portion of the endoscope shown in FIG. 2.
Figure 6:
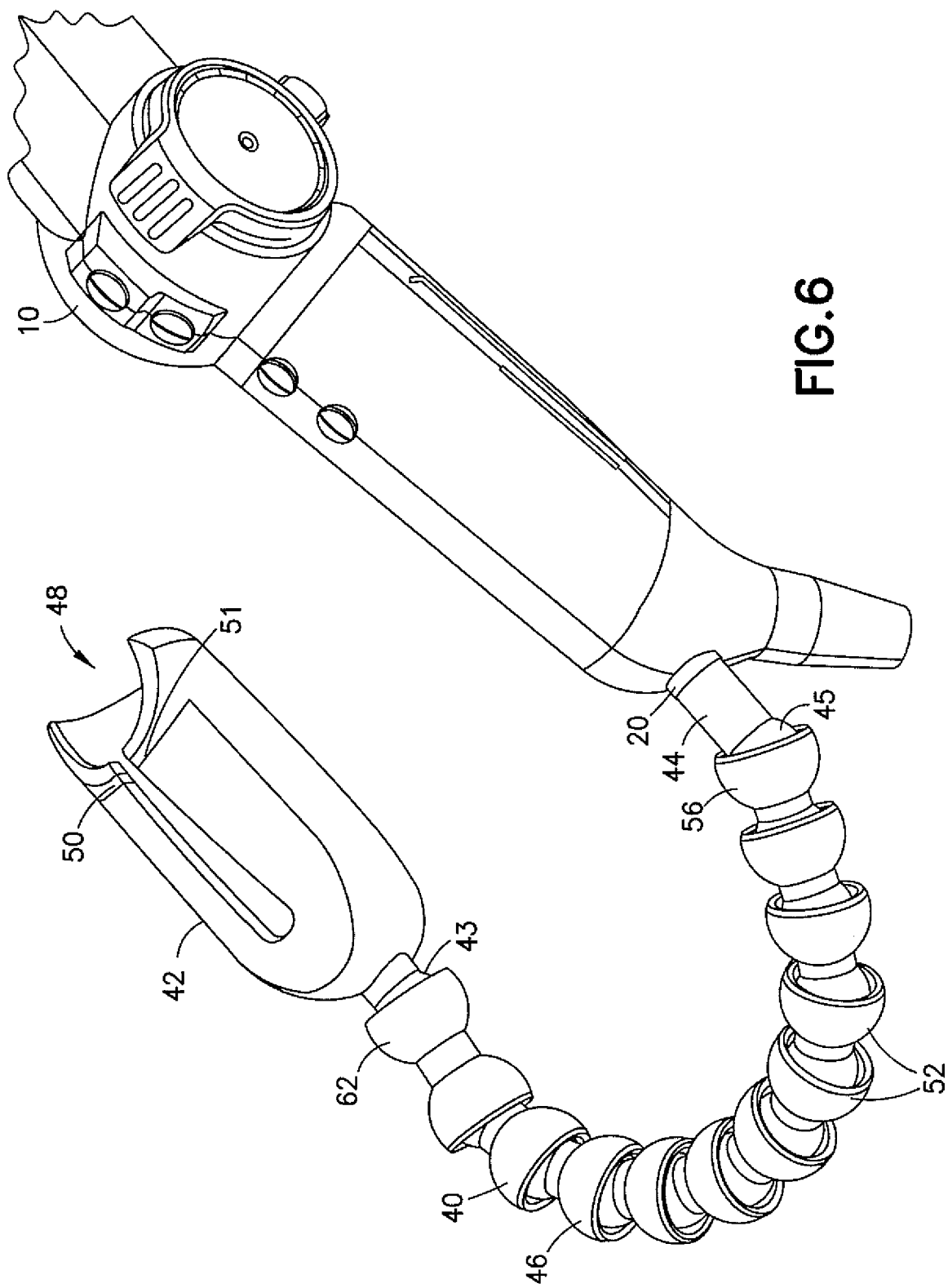
FIG. 6 is a perspective view of the holder and a portion of the endoscope shown in FIG. 2.

Referring also to FIG. 2, one example of a working tool 24 is shown connected to the endoscope 10. In this example embodiment the working tool 24 is a Surgeon Controlled Basket Device (SCBD). However, in alternate examples, any suitable working tool could be provided. The tool 24 includes an assembly 33 which comprises a basket device 32 and a sheath 34. The basket device 32 comprises a basket section at a distal end, and a shaft section extending through the sheath 56 to a handle 36 at a proximal end of the tool 24. The sheath and basket device 32 are longitudinally movable relative to each other to move the basket device between a forward position and a rearward position relative to the sheath 34. In the forward position of the sheath 34 on the basket device 32, the basket section is located inside the sheath 34; the basket section being collapsed by the sheath 34 into a smaller shape to fit inside the sheath 34. A similar working tool is described in U.S. patent application Ser. No. 13/715,091 filed Dec. 14, 2012 which is hereby incorporated by reference in its entirety. The proximal end 36 forms a working handle for the tool 24. The user may move the control lever 38 forward and backward as indicated by arrow A to longitudinally move the sheath 34 and basket device 32 relative to each other.

Figure 7:
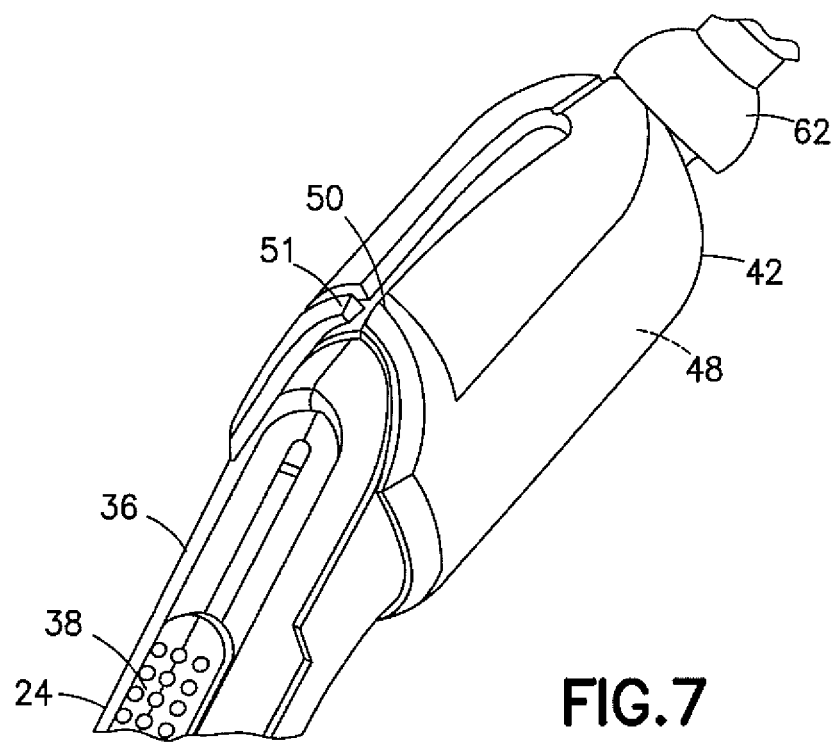
FIG. 7 is a partial perspective view of a connection of the holder to the handle of the working tool shown in FIG. 2.

The apparatus shown in FIG. 2 includes a position holder 40. Referring also to FIGS. 3-6, the position holder 40 generally comprises a first end 42, a second end 44 and a spine 46 connecting the first end 42 with the second end 44. The first end 42 has a pocket 48 which is sized and shaped to receive the proximal end of the working tool's handle 36. The second end 44 is removably connected to the connector 20 at the proximal end of the handle 12. As seen best in FIG. 4, in this example embodiment the second end 44 has a snap-in projection which is snapped into a receiving slot of the connector 20. However, in alternate examples any suitable connection would be provided. Referring also to FIG. 7, in the example shown the first end 42 is adapted to snap-on to the handle 36 with resilient deflection of the arms 50, 51. However, in alternate examples any suitable type of removable connection of the first end 42 to the handle 36 of the tool 24 could be provided.

Figure 8:
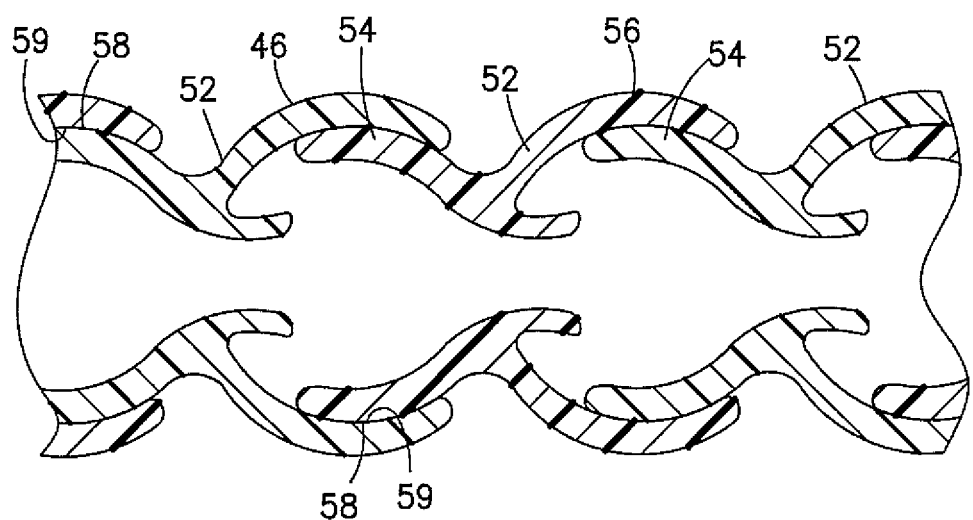
FIG. 8 is a partial cross sectional view of the spine shown in FIG. 3.

The spine 46, in this example, comprises a plurality of vertebrae 52. Each vertebrae 52 is the same in this example comprising a ball section 54 and a socket section 56. Referring also to FIG. 8, the ball sections 54 are received in the adjacent socket section 56 of the next vertebrae 52. Thus, each joint of the spine has a general ball and socket connection. This forms the spine as a plurality of serially interconnected members 52 which are rotatable relative to each other. The connections of the members 52 to one another form friction locks at the joints due to frictional engagement of ball surface 58 with interior socket surface 59. The friction locks are configured to be temporarily unlocked, by overcoming friction forces at the friction locks, such that the spine is semi-flexible. The spine 46 has a connector 62 to connect to a ball section 43 on the first end 42. The second end 44 has a ball section 45 to connect to one of the socket sections 56 of the spine 46.

Figure 9:
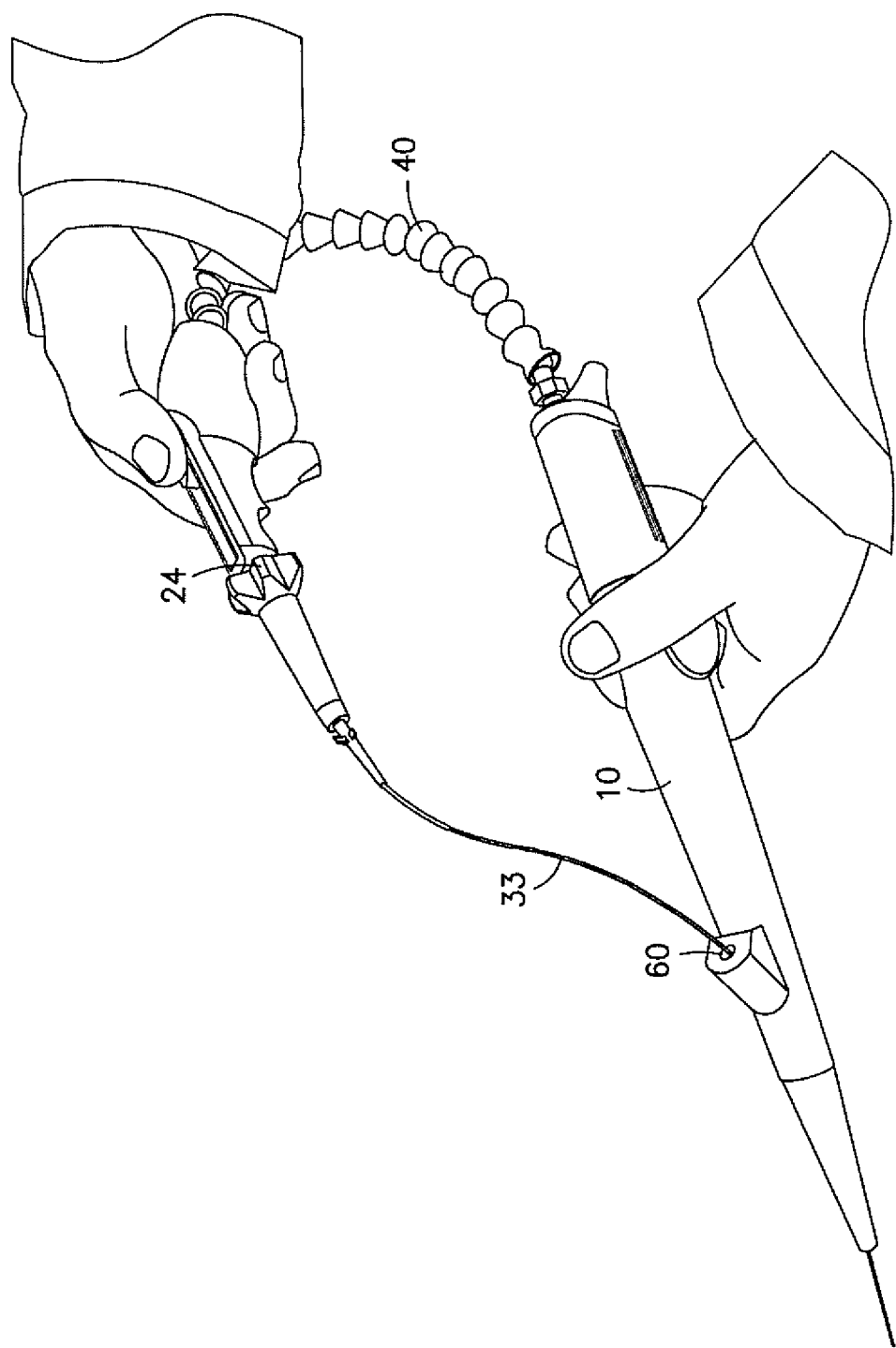
FIG. 9 is a perspective view of a user holding the endoscope and working tool, with the holder attached, shown in FIG. 2.
Figure 10:
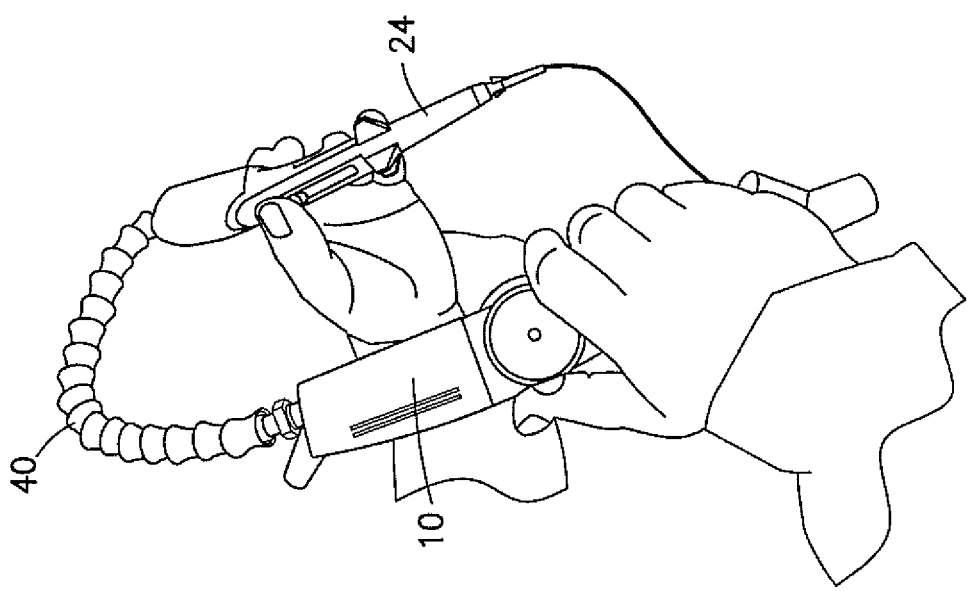
FIG. 10 is a perspective view of a user holding the endoscope and working tool, with the holder attached, shown in FIG. 9 in a different relative position.

Referring also to FIGS. 9-10, the apparatus 10, 24, 40 allows a single user to hold and operate the handle 12 of the endoscope 10 with one hand, and to hold and operate the handle 36 of the working tool with the other hand. The position holder 40 stabilizes the position of the two handles 12, 36 relative to each other while the user manipulates the levers 30, 38. Because the holder 40 is able to hold its shape until moved by the user, because of the frictional locking at the joints of the spine, the user can take his/her hand off of the working tool handle 36 to move the endoscope relative to the patient. The user can position the two handles 12, at any suitable location relative to each other to allow for the most convenient and comfortable use of the two devices 10, 24 at the same time by the single user. Thus, assistance of another surgeon or nurse to hold one of the devices 10, 24 while the user uses the other device is no longer necessary.

Figure 11:
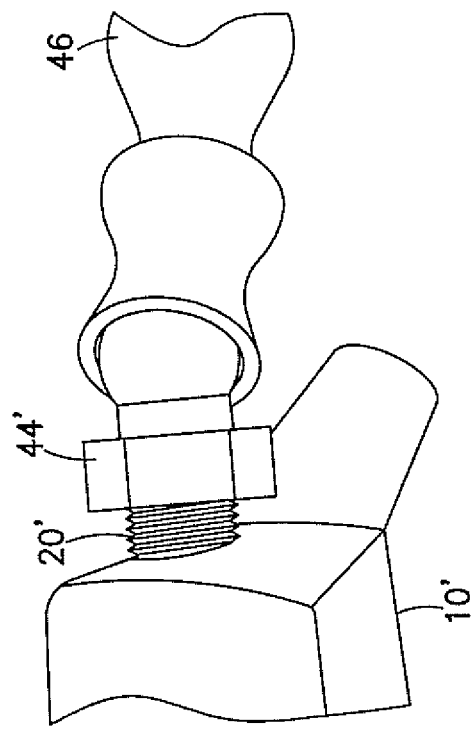
FIG. 11 is a partial view of an alternate example of a connection of the holder to the proximal end of the handle of the endoscope.

Referring also to FIG. 11, an alternate example is shown. In this example embodiment the proximal end of the endoscope 10' comprises a connector 20' having a threaded connection. The connector 44' has a threaded section similar to a nut which is screwed onto the connector 20' in order to removably connect the spine 46 to the handle of the endoscope 10'.

Features as described herein may provide a new snap-on device 40 which includes an ergonomically designed end 42 having a pocket for connection to the handle of a working tool. The end 42 is connected to the one end of the flexible tubing or spine 46. The other side of the spine 46 is configured to be connected with a quick connector to the proximal end of the endoscope 10.

This type of design may provide a "Free style" type of snap-on holder 40 as a disposable device can be used to connect the flexible endoscope and the working tool, such as a stone retrieval basket for example, and allows it to be used easily and conveniently. This device may reduce the surgeon's stress and inconvenience during a urology procedure, does not interfere with other accessories, allows the surgeon to use the tool 24 as it was designed, and easily adjusts for intuitive control. In addition, the device 40 is very simple, inexpensive, could be disposable, requires minimum training and is very easy to use. Using this device 40 allows different positions and orientations for right-hand and left-hand doctors. This "Free style" design allows a surgeon who may be holding endoscope 10 and working tool 24 to use both hands, and to move each hand smoothly with respect to one another to manipulate each tool without causing interruption to the flow of the clinical procedure.

The holder 40 may be a plastic disposable device. An easy and fast connect of the holder 40 to the back of endoscope housing may be provided such as by means of the clip style connection with the connector 20. The holder 40, because of the friction locks, is easy to adjust making convenient orientation for the surgeon. The friction locks make it possible for the surgeon to temporarily release one of two hands for making any additional manipulations, because the friction locks are able to lock in a relative orientation of both instruments with respect to each other. As seen with reference to FIGS. 9-10, the features allow the holder to manipulate the tool 24, such as with the basket in orientation at the distal end of the endoscope for which it was designed. The holder 40 is configured to stay in a stable position in the user selected relative position; relative to the endoscope handle. The holder 40 does not (or minimally) interfere with other different surgical instruments during a procedure. In one type of alternate example, the holder may include a telescoping section for potentially using a telescopic end of the flexible tubing.

An example embodiment may be provided in an apparatus comprising a first end configured to connect to a control of an endoscope object removal tool; a second end having a connector configured to removably connect to a handle of an endoscope; and a spine connecting the first end to the second end, where the spine comprises a plurality of serially interconnected members which are rotatable relative to each other, where connections of the members to one another comprise friction locks, where the friction locks are configured to be temporarily unlocked by overcoming friction forces at the friction locks such that the spine is semi-flexible. The first end may be configured to removably connect to the control of the endoscope object removal tool. The first end may be configured to removably snap onto a proximal end of the endoscope object removal tool. The first end may comprise a pocket configured to receive a portion of a proximal end of the endoscope object removal tool. The pocket may be configured for snap-on attachment and detachment. The pocket may be configured to be ergonomically formed for grasping by a hand of a user. The second end may be configured to removably snap onto the handle of the endoscope. The connections of the members to one another may comprise universally rotatable connections. The universally rotatable connections may comprise ball and socket connections. The apparatus may further comprise an endoscope object removal tool connected to the first end.

An example method may comprise providing a spine comprising a plurality of serially interconnected members which are rotatable relative to each other, where connections of the members to one another comprise friction locks, where the spine is semi-rigid and is reconfigurable to different semi-rigid shapes; connecting a first connector to a first end of the spine, where the first connector is sized and shaped to removably connect to a control of an endoscope object removal tool; and connecting a second connector to an opposite second end of the spine, where the second connector is sized and shaped to removably connect to a handle of an endoscope.

The spine may be provided such that the friction locks are configured to be temporarily unlocked by overcoming friction forces at the friction locks. The first end may be configured to removably snap onto a proximal end of the endoscope object removal tool. The first end may comprise a pocket configured to receive a portion of a proximal end of the endoscope object removal tool. The second end may be configured to removably snap onto the handle of the endoscope. The connections of the members to one another may be provided as universally rotatable connections. The universally rotatable connections may be provided as ball and socket connections. The method may further comprise connecting an endoscope object removal tool to the first end.

An example method may comprise connecting a first end of an accessory to a handle of an endoscope; connecting a second end of the accessory to a control of an endoscope object removal tool; and reconfiguring a shape of a semi-rigid spine of the accessory from a first configuration to a second configuration, where the semi-rigid spine connects the first end to the second end, and where the semi-rigid spine retains the relative location of the first and second ends at the first configuration and retains the relative location of the first and second ends at the second configuration.

Connecting the first end of the accessory to the handle of the endoscope may comprise removably connecting the first end to the handle. Removably connecting the first end to the handle may comprise snapping the first end onto a portion of the handle. Connecting the second end of the accessory to the control of the endoscope object removal tool may comprise removably connecting the second end of the accessory to the control of the endoscope object removal tool. Removably connecting the second end of the accessory to the control of the endoscope object removal tool may comprise snapping the second end onto a portion of the control.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:
1. An apparatus comprising:
a first end configured to connect to a control of an endoscope object removal tool, where the first end comprises a pocket configured to receive a portion of the endoscope object removal tool, where the pocket comprises an entrance in a front end of the pocket, a rear end which is closed and deflectable sides to resiliently deflect to hold the endoscope object removal tool when the endoscope object removal tool is inserted into the entrance, wherein the first end comprises a one-piece member, wherein the resiliently deflectable sides are adapted to snap on to a proximal end of a handle of the endoscope object removal tool without another member therebetween, and wherein the pocket and the resiliently deflectable sides are adapted to snap on to the endoscope object removal tool such that a majority of the endoscope object removal tool extends distally beyond the entrance of the pocket;
a second end having a connector configured to be received into a slot on a handle of an endoscope and retained therein to removably connect the second end to the endoscope; and
a spine connecting the first end to the second end, where the spine is connected to the first end by a connection at a portion of the first end which forms the closed rear end of the pocket, where the spine comprises a plurality of serially interconnected members which are rotatable relative to each other using connections in which a flexing movement of the members is limited by an engagement of an outer surface of each of the members with an interior surface of a successive member, where connections of the members to one another comprise friction locks, where the friction locks are configured to be temporarily unlocked by overcoming friction forces at the friction locks such that the spine is semi-flexible.

2. An apparatus as in claim 1 where the first end is configured to removably connect to the control of the endoscope object removal tool.

3. An apparatus as in claim 1 where the first end is configured to removably snap onto the proximal end of the endoscope object removal tool.

4. An apparatus as in claim 1 where the pocket is configured for snap-on attachment and detachment.

5. An apparatus as in claim 1 where the pocket is configured to be ergonomically formed for grasping by a hand of a user.

6. An apparatus as in claim 1 where the second end is configured to removably snap onto the handle of the endoscope.

7. An apparatus as in claim 1 where the connections of the members to one another comprise universally rotatable connections.

8. An apparatus as in claim 7 where the universally rotatable connections comprise ball and socket connections.

9. An apparatus as in claim 1 further comprising an endoscope object removal tool connected to the first end.

10. A method comprising:
providing a spine comprising a plurality of serially interconnected members which are rotatable relative to each other using connections in which a flexing movement of the interconnected members is limited by an engagement of an outer surface of each of the members with an interior surface of a successive member, where connections of the interconnected members to one another comprise friction locks, where the spine is semi-rigid and is reconfigurable to different semi-rigid shapes;
connecting a first connector to a first end of the spine, where the first connector is sized and shaped to removably connect to a control of an endoscope object removal tool, where the first connector comprises a pocket configured to receive a portion of the endoscope object removal tool, where the pocket comprises an entrance in a front end of the pocket, a rear end which is closed and deflectable sides to resiliently deflect to hold the endoscope object removal tool when the endoscope object removal tool is inserted into the entrance, wherein the first connector comprises a one-piece member, wherein the resiliently deflectable sides are adapted to snap on to a proximal end of a handle of the endoscope object removal tool without another member therebetween, where the spine is connected to the first connector by a connection at a portion of the first connector which forms the closed rear end of the pocket, and wherein the pocket and the resiliently deflectable sides are adapted to snap on to the endoscope object removal tool such that a majority of the endoscope object removal tool extends distally beyond the entrance of the pocket; and
connecting a second connector to an opposite second end of the spine, where the second connector is sized and shaped to be received into a slot on a handle of an endoscope and retained therein to removably connect the second end to the endoscope.

11. A method as in claim 10 where the spine is provided such that the friction locks are configured to be temporarily unlocked by overcoming friction forces at the friction locks.

12. A method as in claim 10 where the first connector is configured to removably snap onto a proximal end of the endoscope object removal tool.

13. A method as in claim 10 where the second connector is configured to removably snap onto the handle of the endoscope.

14. A method as in claim 10 where the connections of the interconnected members to one another are provided as universally rotatable connections.

15. A method as in claim 14 where the universally rotatable connections are provided as ball and socket connections.

16. An apparatus as in claim 1 where the connection of the spine to the first end is in-line with the pocket.

17. An apparatus comprising:
a first end configured to connect to a control of an endoscope object removal tool, wherein the first end comprises a one-piece member having resiliently deflectable sides adapted to snap on to a proximal end of a handle of the endoscope object removal tool without another member therebetween, and wherein a pocket and the resiliently deflectable sides are adapted to snap on to the endoscope object removal tool such that a majority of the endoscope object removal tool extends distally beyond the entrance of the pocket;
a second end having a connector configured to be received into a slot on a a handle of an endoscope and retained therein to connect the second end to the endoscope, where the second end is configured to be connected to a rear end of the handle of the endoscope such that the second end extends away from the rear end of the handle substantially in-line with the rear end of the handle; and
a spine connecting the first end to the second end, where the spine comprises a plurality of serially interconnected members which are rotatable relative to each other using connections in which a flexing movement of the members is limited by an engagement of an outer surface of each of the members with an interior surface of a successive member, where connections of the members to one another comprise friction locks, where the friction locks are configured to be temporarily unlocked by overcoming friction forces at the friction locks such that the spine is semi-flexible.

18. An apparatus as in claim 17 where the second end comprises a projection configured to be inserted into the slot at the rear end of the handle of the endoscope.

19. A method as in claim 10 where the connection of the spine to the first connector is in-line with the pocket.

20. A method as in claim 10 where the second connector is configured to be connected to a rear end of the handle of the endoscope such that the second end extends away from the rear end of the handle substantially in-line with the rear end of the handle.

* * * * *